United States Patent [19]

Grischenko et al.

[11] Patent Number: 4,965,186

[45] Date of Patent: Oct. 23, 1990

[54] METHOD FOR LOW-TEMPERATURE PRESERVATION OF SPERMATOZOA

[76] Inventors: Valentin I. Grischenko, ulitsa Pushkinskaya, 67/69, kv. 31; Jury V. Kalugin, ulitsa Krasmoznamennaya, 6, kv. 24; Jury S. Paraschuk, ulitsa Pushkinskaya, 67/69, kv. 30; Nina A. Luchko, ulitsa Dokuchaeva, 34; Elena N. Chernysh, ulitsa Chkalova, 13, kv. 26; Valery F. Tarasov, ulitsa S. Esenina, 19, kv. 40; Sergei E. Galchenko, ulitsa Korchagintsev, 36, kv. 17, all of Kharkov, U.S.S.R.

[21] Appl. No.: 209,574

[22] Filed: Jun. 21, 1988

[51] Int. Cl.$^5$ .............................................. A01N 1/02
[52] U.S. Cl. ..................................................... 435/2
[58] Field of Search ............................ 424/105; 435/2

[56] References Cited

U.S. PATENT DOCUMENTS 3,185,623  5/1965  Smith et al. ............................ 435/2
3,791,384  2/1974  Richter et al. ......................... 435/2

OTHER PUBLICATIONS

Sherman–Fertility and Sterility vol. 14, No. 1 (1963), pp. 49–64.
Nauk et al.–Chem. Abst. vol. 102 (1985), p. 110, 595e.

*Primary Examiner*—Sam Rosen
*Attorney, Agent, or Firm*—Ladas & Parry

[57] ABSTRACT

The method resides in cooling the spermatozoa in a high thermal-diffusive powdered material that has preliminarily been cooled down to the refrigerant temperature. Cooling is carried out in a medium of a cryopreservative, containing a salt buffer, an antishock component, and a cryoprotector. The cryoprotector is taken in a concentration high enough for vitrification to develop in the spermatozoa. An example of the high thermal diffusive powdered material is alumina.

5 Claims, No Drawings

METHOD FOR LOW-TEMPERATURE PRESERVATION OF SPERMATOZOA

FIELD OF THE INVENTION

The present invention relates to cryobiology and cryomedicine and has particular usefulness as a method for low-temperature preservation of spermatozoa.

The present invention can find the most utility when applied to deep freezing of human spermatozoa intended for clinical use in treatment of infertility, thereby contributing to building-up of low-temperature banks of spermia, thus enabling their selection in terms of quality of frozen cells. Besides, use of frozen spermatozoa is now highly efficacious in treatment of various forms of infertility by virtue of extracorporeal fertilization of an ovum.

The invention can also find application in some other domains of cryobiology, e.g., in farming practice for breeding novel races of farm animals within the shortest possible time period. Low-temperature preservation of spermatozoa of commercial, valuable and rare fish species is also one of the measures for their rapid reproduction. Thus, application of low temperature techniques for low-temperature preservation of spermatozoa is covering still more and more spheres of man's economic activity and of public health protection.

Widespread application found nowadays by freezing of spermatozoa has made it necessary to further improve methods of their preservation, since the heretofore-existing methods fail to afford adequate cryoprotection of spermia due to development of the crystallization process which eventually results in loss of the penetrating ability by some of the frozen cells. Thus, further development of the methods for cryopreservation of spermatozoa on the basis of vitrification, aimed at increasing their survivability has become evident.

DESCRIPTION OF THE PRIOR ART

One prior-art method for freezing of spermatozoa is to add dropwise anhydrous glycerol to the ejaculate till a final concentration of 10 percent is obtained (cf. Fertil. and Steril., v. 14, No. 1, 1963. I. K. Sherman "Improved Methods of Preservation of Human Spermatozoa by Freezing and Freeze-Drying"). After dispensing the spermatozoa along with the cryoprotector by 0.5-ml portions in glass or polyethylene ampoules and thereafter hermetically sealing, the spermatozoa are cooled down to minus 75° C. at a rate of 25° C. per minute, then to minus 180° C. at a rate of 16° C. The survival rate of the spermia after thawing is as low as 60 percent.

Disadvantages inherent in the aforesaid method reside in osmotic damage to the cells due to direct addition of glycerol to the ejaculate. Latent injuries inflicted thereby upon the cell membrane apparatus, especially on its acrosomal cap, are aggravated in the course of cooling, thus causing irreversible damage to the biological structures in the majority of the cells involved.

Also known in the art is a method for low-temperature preservation of spermatozoa with a cryoprotector in the form of granules by installing the spermatozoa into depressions made on the surface of carbon-dioxide ice (cf. Treatment of Male Infertility, 1982, Berlin - Heidelberg - New York; I. Barkay, H. Zuckerman, 'Cryopreservation and Pooling of Spermatozoa', pp. 263-281). The freezing process of 0.1-0.15-ml specimens proceeds in this case at a very high rate within 60 seconds. To freeze spermatozoa in granules use is made of a special device provided with a temperature-controlled cabinet with which the low-temperature freezing process is controlled. The survival rate of the spermatozoa thus treated reaches 70 to 75 percent.

A disadvantage of the method lies with the fact that freezing of spermatozoa is accompanied by the crystallization process so that the spermatozoa are frozen in the shape of a sphere. As a result, a temperature gradient arises in the spermatozoa specimen being frozen due to different rates of cooling of the cells located at the center of a depression and close to its walls, whereby freezing of spermatozoa in granules cannot be performed aseptically.

Another method for low-temperature preservation of spermatozoa is known from (U.S. Pat. No. 1,103,837), wherein a cryoprotector, viz., glycerol is slowly added to the spermatozoa being treated until a final concentration of 10 percent is obtained, whereupon the spermatozoa are dispensed in 0.5-ml sterile tubes and the latter are sealed hermetically. Freezing is carried out in two stages, first to 4° or 5° C. at a rate of 0.5° to 1.0° C. per minute, after which the spermatozoa are held at that temperature for 30 to 60 minutes; then freezing proceeds at a rate of 20° to 25° C. per minute until a temperature of minus 180° to 190° is obtained. The thus-frozen spermatozoa are kept stored in liquid nitrogen and thawed in a water bath at 36° C. The survival rate of spermatozoa equals 66 percent.

A disadvantage of the aforementioned method resides in that low-temperature preservation of spermia is accompanied by the crystallization process the development of which is retarded by the freezing conditions that are not however causative of vitrification. Besides, positive influence of the cryoprotector on said process is countervailed by the negative phenomena concerned with direct addition of 10-percent glycerol to the ejaculate. This results in injury to the cytoplasmic membrane of the spermia and hence in reduced cryoresistance of said membrane. In addition, direct addition of anhydrous glycerol to spermatozoa leads to powerful osmotic shifts in the ejaculate. In this case drastic dehydration of the cells causes partial denaturation of the protein molecules and disorientation of the cell organelles. When the cell has prolonged exposure to a high-concentration glycerol medium there is concern with the manifestation of a toxic effect of said cryoprotector.

OBJECT AND SUMMARY OF THE INVENTION

It is an object of the present invention to provide a higher survival rate of the spermia being treated.

It is another object of the present invention to provide a simpler process for low-temperature preservation of spermatozoa as a whole.

A further object of the present invention is to provide a shorter cycle of low-temperature preservation of spermatozoa.

A still further object of the present invention is to provide high labor productivity involved in realization of the method for low-temperature preservation of spermatozoa.

It is yet still one more object of the present invention to make the method less expensive.

The foregoing and other objects of the present invention are accomplished due to the fact that in a method for low-temperature preservation of spermatozoa, comprising introduction of a cryoprotector into the spermatozoa and their cooling down to the refrigerant temperature, according to the invention, a salt buffer and an antishock component are introduced into the spermatozoa, both of them forming, together with the cryoprotector preservative, and the spermatozoa are cooled in a medium of the cryopreservative placed in a high thermal-diffusive powdered material which has preliminarily been cooled down to the refrigerant temperature, while the concentration of the cryopreservative is high enough for the noncrystalline phase to develop in the course of freezing the spermatozoa and the cryopreservative.

The proposed method makes it possible to attain a higher effect of the morphofunctional preservation of the spermia by developing vitrification, which enables as high as 85-percent rate of their survival to be attained. This can be achieved due to the use for cooling the spermatozoa, of a high thermal-diffusive powdered material which rules out formation of a heat-insulating shell of the refrigerant vapor round the object being cooled due to the absence of a direct contact between the object and the refrigerant. The resultant considerable increase in the cooling rate proves to be sufficient for vitrification to develop and makes it possible to reduce the cryoprotector concentration to a value which will contribute to realization of said process.

The proposed method makes it possible to avoid the development of the crystallization process in the spermatozoa being frozen and hence to rule out any extreme factors that foster that process.

At the same time the proposed method makes it possible to simplify the low-temperature preservation process due to a reduced number of operations and shorter time for their performing. Alongside of the foregoing the present invention is instrumental to higher labor productivity and lower prime cost of the method due to cutting down the cycle of the low-temperature preservation.

According to the preferred embodiment of the invention alumina ($Al_2O_3$) is used as the high thermal-diffusive powdered material. This is concerned with the fact that a cooling rate high enough for noncrystalline freezing is developed to provide vitrification of the spermia in a medium of the proposed cryopreservative, which is accounted for by relatively small size of said cells as compared with some other ones, in particular, embryos and hence by a less amount of free water in the spermia to be frozen.

It is quite expedient that the cryoprotector be used in a concentration of from 1.5 to 2.5 percent, since neither toxic nor osmotic properties of the cryoprotector manifest themselves with such a concentration thereof, though the latter is high enough for the development of vitrification under the preselected cooling conditions.

According to one of the embodiments of the invention the cryopreservative contains a biologically potent substance.

Biologically potent substances are made use of in cryopreservation of spermatozoa with a view to increasing the survival rate of the cells being treated by affording protection to the cell cytoplasmic membrane against the temperature shock and the "solution effect" during the phase transition into ice.

It is expedient that choline chloride be used as the biologically potent substance.

Choline chloride serving as a methylating agent in biologic processes due to high energy potential of the nitrogen group, the presence of three methyl groups and one hydroxyl group, is featured by high basicity which brings about active hydration of the water molecules by the substance involved, thus adding to the cryoprotective properties of the cryopreservative. Methyl groups stabilize the native structure of biomembranes, thus adding to their cryoresistance.

It is quite expedient that choline chloride be used in a concentration of 2 percent.

A lower choline-chloride concentration fails to afford higher cryoprotective efficacy of the cryopreservative, while higher concentrations of that biologically potent compound add to its hydrophobic interaction with biomacromolecules, which results in alteration to the membrane structure rather than in stabilization of the membranes.

Further objects and advantages of the present invention will become obvious from a detailed description of the specific embodiment thereof that follow.

BRIEF DESCRIPTION OF THE EMBODIMENTS

To carry the method into effect a metallic vessel is immersed in the refrigerant, viz., liquid nitrogen, said vessel being filled with the high thermal-diffusive powdered material into which the container holding the diluted spermatozoa is plunged.

The method of the invention is carried out as follows. Once diluted the spermatozoa are mixed with the cryopreservative which is in effect an aqueous solution containing glucose, sodium citrate, i.e., the salt buffer, an egg yolk as the antishock component, a biologically potent substance, viz., a choline-chloride solution, and a cryoprotector, i.e., glycerol. The diluted spermatozoa are subjected to equilibration and then dispensed in containers made from food packing foil, which are then flared out and plunged into the high thermal-diffusive powdered material cooled down to the temperature of the refrigerant, i.e., liquid nitrogen, then the containers are quickly transferred to liquid nitrogen for being stored there. The thus-frozen spermatozoa are thawed out in a water bath.

EXAMPLE 1

2 ml of spermatozoa is placed for 25 to 30 minutes in a thermostat at 37° C. for dilution, whereupon an agent is added in a 1:1 ratio containing 4.0 g of glucose, 1.2 g of sodium citrate, 26.0 ml of egg yolk, 2.0 ml of a 20-percent choline-chloride solution, and 3.0 ml of glycerol, water being the balance. The final glycerol concentration equals 1.5 percent. The thus-thinned spermatozoa are kept for 45 minutes, then dispensed by 0.5 ml in containers made of food packing foil having a wall thickness of 0.3 mm, whereupon the free edges of the containers are flared out. To freeze the spermatozoa the containers are plunged into a freezing chamber, which is in fact a metallic vessel filled with powdered alumina and immersed in liquid nitrogen, whereupon the containers are held in powdered alumina for 5 to 10 seconds and then are transferred in liquid nitrogen for being stored there.

Thawing is carried out three weeks after cryopreservation by immersing the container in a water bath at 40° C. After being thawed out the pH of the spermatozoa equals 7.5; a total number of the spermia, 52 millions per milliliter, motility, 66 percent; active motility, 51.8 percent; normal forms, 72 percent.

The survival rate of the spermatozoa is determined according to the formula:

$$\frac{\% \text{ of spermia motile after having been thawed out}}{\% \text{ of spermia before freezing}} \times 100$$

according to the results obtained it is equal to 82.2 percent.

EXAMPLE 2

2 ml of spermatozoa is placed for 25 to 30 minutes in a thermostat at 37° C. for dilution, whereupon an agent is added in a 1:1 ratio, containing 4.0 g of glucose, 1.2 g of sodium citrate, 26.0 ml of egg yolk, 2.0 ml of a 20-percent choline-chloride solution, and 4.0 ml of glycerol, water being the balance. The final glycerol concentration is 2.0 percent. The thinned spermatozoa are kept for 45 minutes and then dispensed by 0.5 ml in containers made of food packing foil and having a wall thickness of 0.3 mm, whereupon the free edges of the containers are flared out. To freeze the spermatozoa the containers are plunged into a freezing chamber, which is in fact a metallic vessel filled with powdered alumina and immersed in liquid nitrogen, whereupon the containers are held in powdered alumina for 5 to 10 seconds and then are transferred in liquid nitrogen for being stored there.

Thawing is carried out three weeks after cryopreservation by immersing the container in a water bath at 40° C. After being thawed out the spermatozoa have the pH value of 7.5; a total number of the spermia, 52 millions per milliliter; motility, 66 percent; active motility, 53.1 percent; normal forms, 72 percent.

The survival rate of the spermatozoa is determined according to the formula:

$$\frac{\% \text{ of spermia motile after having been thawed out}}{\% \text{ of spermia motile before freezing}} \times 100;$$

according to the results obtained it is equal to 84.2 percent.

EXAMPLE 3

2 ml of spermatozoa is placed for 25 to 30 minutes in a thermostat at 37° C. for dilution, whereupon an agent is added in a 1:1 ratio, containing 4.0 g of glucose, 1.2 g of sodium citrate, 26.0 ml of egg yolk, 2.0 ml of a 20-percent choline-chloride solution, and 5.0 ml of glycerol, water being the balance. The final glycerol concentration is 2.5 percent. The thinned spermatozoa are kept for 45 minutes and then dispensed by 0.5 ml in containers made of foodstuff foil and having a wall thickness of 0.3 mm, whereupon the free edges of the containers are flared out. To freeze the spermatozoa the containers are plunged into a freezing chamber, which is in fact a metallic vessel filled with powdered alumina and immersed in liquid nitrogen, whereupon the containers are held in powdered alumina for 5 to 10 seconds and then are transferred in liquid nitrogen for being stored there.

Thawing is carried out three weeks after cryopreservation by immersing the container in a water bath at 40° C. After being thawed out the spermatozoa have the pH value of 7.5; a total number of the spermia, 52 millions per milliliter; motility, 66 percent; active motility, 54.7 percent; normal forms, 72 percent.

The survival rate of the spermatozoa is determined according to the formula:

$$\frac{\% \text{ of spermia motile after having been thawed out}}{\% \text{ of spermia motile before freezing}} \times 100;$$

according to the results obtained it is equal to 86.5 percent.

To corroborate the fact that use of a reduced glycerol concentration within the specified limits and of high-rate freezing in a medium of powdered alumina make it possible to attain the object of the invention, given below are the tabulated results of the experiments performed, the results of the aforestated examples inclusive.

TABLE 1

Survival rate of spermia undergone low-temperature preservation vs the composition of the freezing medium

| Nos | Glycerol concentration, % | Survival rate of spermia, % |
|---|---|---|
| 1 | Native spermatozoa free from cryopreservative and glycerol | 37.5 ± 1.46 |
| 2 | Spermatozoa with cryopreservative but less glycerol | 49.1 ± 2.18 |
| 3 | 1.0 | 67.2 ± 3.18 |
| 4 | 1.5 | 82.2 ± 2.22 |
| 5 | 2.0 | 84.2 ± 1.81 |
| 6 | 2.5 | 86.8 ± 1.16 |
| 7 | 3.0 | 78.2 ± 1.17 |
| 8 | 5.0 | 71.0 ± 3.18 |

TABLE 2

Motility of spermia vs the freezing medium.

| Nos | Glycerol concentration, % | Survival rate of sperma % |
|---|---|---|
| 1 | Native spermatozoa free from cryopreservative and glycerol | 22.5 ± 1.36 |
| 2 | Spermatozoa with cryopreservative but less glycerol | 28.0 ± 2.16 |
| 3 | 1.0 | 42.0 ± 2.86 |
| 4 | 1.5 | 51.8 ± 1.12 |
| 5 | 2.0 | 53.1 ± 2.16 |
| 6 | 2.5 | 54.7 ± 1.61 |
| 7 | 3.0 | 50.2 ± 1.56 |
| 8 | 5.0 | 44.0 ± 2.74 |

TABLE 3

Motility of spermia vs the methods for low-temperature preservation of spermatozoa

| Preservation method | Motility of spermia | |
|---|---|---|
| | before preservation | after thawing |
| Herein-proposed | 64.1 ± 3.18 | 54.68 ± 1.12 |
| Heretofore-known | 65.11 ± 3.64 | 43.67 ± 2.47 |
| | | $p < 0.05$ | p - reliability index of differences in statistic processing according to student-Fisher.

The data tabulated above evidence that motility of the thawed-out spermia in both cases is reduced as compared with their motility before freezing. However, the proposed method makes it possible to obtain spermatozoa having higher activity compared with the known method.

The examples adduced hereinbefore indicate that the lowest results are obtained when native spermatozoa are subjected to cryopreservation. Addition of a cryopreservative free from glycerol somewhat increases the degree of preservation of the cells. More pronounced is cryoprotection afforded by a cryopreservative incorporating glycerol, the maximum degree of cryoprotection being afforded when the glycerol concentration in the freezing medium is within 1.5 and 2.5 percent. Use of glycerol in a 2.5-percent concentration in the present method of freezing makes it possible to increase the survival rate by 19.8 percent, which is a very positive rate of the spermia preservation.

Thus, the presence of low-concentration glycerol to the cryopreservative, as well as choline chloride establishes favourable conditions therein for exhibition of a maximally pronounced cryoprotective efficacy free from any negative phenomena.

This is demonstrated particularly by the fact that the cells in the cryopreservative applied feature higher vitality compared with the native material.

What is claimed is:

1. A method for cooling spermatozoa to the temperature of a refrigerant in which they are to be stored comprising:

adding said spermatozoa to a cryopreservative; said cryopreservative comprising a salt buffer, an antishock component, and a cryoprotector, placing said spermatozoa in said cryopreservative into a container made of food packing foil;

introducing said container with said spermatozoa into a thermal diffusive powdered material;

said powdered material having been cooled to the temperature of the refrigerant;

said powdered material being alumina ($Al_2O_3$).

2. A method as claimed in claim 1, wherein the cryoprotector is used in a concentration of from 1.5 to 2.5 percent.

3. A method as claimed in claim 1, wherein the cryopreservative contains choline chloride.

4. A method as claimed in claim 3, wherein choline chloride is taken in a concentration of 2 percent.

5. A method as in claim 1, wherein the antishock component is egg yolk.

* * * * *